(12) United States Patent
Miller

(10) Patent No.: US 6,488,499 B1
(45) Date of Patent: Dec. 3, 2002

(54) METHODS FOR CORRECTING DEVIATIONS IN PREPLANNED TOOTH REARRANGEMENTS

(75) Inventor: Ross Miller, Sunnyvale, CA (US)

(73) Assignee: Align Technology, Inc., Santa Clara, CA (US)

( * ) Notice: Subject to any disclaimer, the term of this patent is extended or adjusted under 35 U.S.C. 154(b) by 46 days.

(21) Appl. No.: 09/843,247

(22) Filed: Apr. 25, 2001

Related U.S. Application Data

(60) Provisional application No. 60/199,465, filed on Apr. 25, 2000.

(51) Int. Cl.[7] .............................................. A61C 3/00
(52) U.S. Cl. ...................................................... 433/24
(58) Field of Search ....................................... 433/6, 24

(56) References Cited

U.S. PATENT DOCUMENTS

| | | | | |
|---|---|---|---|---|
| 3,984,915 A | * | 10/1976 | Noble et al. | 433/24 |
| 4,348,178 A | * | 9/1982 | Kurz | 433/6 |
| 5,975,893 A | * | 11/1999 | Chishti et al. | 433/24 |
| 6,315,553 B1 | * | 11/2001 | Sachdeva et al. | 433/24 |

* cited by examiner

Primary Examiner—John J. Wilson
(74) Attorney, Agent, or Firm—Townsend and Townsend and Crew LLP; Bao Tran, Esq.

(57) ABSTRACT

Orthodontic treatment is achieved using a series of successive, removable repositioning appliances, such as thin polymeric shell appliances referred to as aligners. A set of aligners is originally provided to the patient. If the patient's treatment goes off course using the original set of aligners, further aligners are designed and fabricated to move the deviant tooth arrangement back to a target tooth arrangement which was part of the original treatment program.

6 Claims, 3 Drawing Sheets

METHODS FOR CORRECTING DEVIATIONS IN PREPLANNED TOOTH REARRANGEMENTS

CROSS-REFERENCES TO RELATED APPLICATIONS

This application claims the benefit under 37 CFR §1.78 (a)(3) of prior provisional application No.: 60/199,465, filed on Apr. 25, 2000, the full disclosure of which is incorporated herein by reference.

BACKGROUND OF THE INVENTION

1. Field of the Invention

This invention relates in general to a method of repositioning teeth for use in orthodontic treatment. Particularly, this invention relates to the use of orthodontic appliances for producing tooth movements. More particularly, this invention relates to the use of a plurality of elastic repositioning appliances for producing such tooth movements.

Orthodontic treatments involve repositioning misaligned teeth and improving bite configurations for improved cosmetic appearance and dental function. Repositioning teeth is accomplished by applying controlled forces to the teeth over an extended period of time. This is conventionally accomplished by wearing what are commonly referred to as "braces." Braces comprise a variety of appliances such as brackets, bands, archwires, ligatures, and O-rings. After they are bonded to the teeth, periodic meetings with the orthodontist are required to adjust the braces. This involves installing different archwires having different force-inducing properties or by replacing or tightening existing ligatures. Between meetings, the patient may be required to wear supplementary appliances, such as elastic bands or headgear, to supply additional or extraoral forces.

Although conventional braces are effective, they are often a tedious and time consuming process requiring many visits to the orthodontists office. Moreover, from a patient's perspective, they are unsightly and uncomfortable. Consequently, alternative orthodontic treatments have developed. A particularly promising approach relies on the use of elastic positioning appliances for realigning teeth. Such appliances may comprise a thin shell of elastic material, referred to as an "aligner", that generally conforms to a patient's teeth but is slightly out of alignment with the initial tooth configuration. Placement of an aligner over the teeth applies controlled forces in specific locations to gradually move the teeth into the new configuration. Repetition of this process with successive appliances comprising new configurations eventually move the teeth through a series of intermediate arrangements to a final desired arrangement. A full description of an exemplary elastic polymeric positioning appliance is described in U.S. Pat. No. 5,975,893, and in published PCT application WO 98/58596 which designates the United States and which is assigned to the assignee of the present invention. Both documents are incorporated by reference for all purposes.

Systems of preformed aligners employing technology described in U.S. Pat. No. 5,975,893, are commercially available from Align Technology, Inc., Santa Clara, Calif., under the tradename Invisalign® System. Align Technology, Inc., is the assignee of the present application. The Invisalign® System relies on designing and fabricating at least most of the aligners to be worn by the patient at the outset of treatment. The design of the aligners relies on computer modeling of a series of successive tooth arrangements, and the individual aligners are designed to be worn over the teeth and to elastically reposition the teeth to each of said tooth arrangements. Usually, the set of aligners which is designed and fabricated at the outset of the treatment is able to successfully reposition the teeth to a final desired arrangement. In some cases, however, the treatment deviates from the planned movement stages making continued treatment with the previously provided set of aligners difficult or impossible. Such deviations can arise from biological variations in the individual patient, poor patient compliance, or other factors. The deviations will usually become apparent when the next aligner to be worn in the set of successive aligners does not fit. A poor fit indicates that the tooth arrangement has not progressed to the desired intermediate stage and that the teeth are not ready for the next aligner.

When such deviations occur, the response has usually been to start over with whatever actual tooth arrangement that has been received being the starting point. Aligners are then planned and fabricated to bring the teeth from the actual intermediate arrangement to the desired final arrangement, which is usually the same final arrangement as was the target of the original set of aligners. Starting over, however, can be inefficient and wasteful. Relatively large numbers of aligners can be required, and the remaining aligners in the original set will usually be wasted.

For these reasons, it would be desirable to provide alternative and/or improved methods for making mid-course corrections in orthodontic treatment utilizing sets of aligners or other repositioning appliances which are removable and successively worn by a patient to effect a course of orthodontic treatment. It would be particularly desirable if such methods did not require disposal of all or some of the aligners from the original set and were relatively easy to implement with minimum patient inconvenience. At least some of these objectives will be met by the inventions described hereinafter.

2. Description of the Background Art

U.S. Pat. No. 5,975,893, and published PCT application WO98/58596, have been described above. Co-pending application Ser. No. 09/616,830, relates to the fabrication of orthodontic aligners having varying elastic moduluses. The full disclosures of each of these patents and pending applications are incorporated herein by reference.

BRIEF SUMMARY OF THE INVENTION

According to the present invention, an improved method for repositioning teeth is provided. The method for repositioning generally relies on use of an original set of removable positioning appliances, typically aligners as described in U.S. Pat. No. 5,975,893, the full disclosure of which has been previously incorporated herein by reference. The aligners or other appliances are shaped to move teeth through a plurality of predetermined successive arrangements corresponding to the shape of each appliance. That is, the appliances will be configured to apply repositioning forces to the teeth so that the teeth are moved to an arrangement which closely conforms to the unstressed geometry of the aligner. Thus, after a patient has completed wearing any individual aligner or other appliance, it will be expected that the tooth arrangement will match the shape of the aligner or appliance and that the teeth will be ready to receive a next successive aligner or other appliance. The next successive aligner will be shaped slightly differently from the immediately prior aligner, and it is this difference in shape that will move the teeth still further to their next arrangement. Wearing of successive aligners or other appliances thus can effect an entire course of orthodontic treatment as the teeth are moved through a series of predetermined successive arrangements.

In the case of the Invisalign® System, an original set of aligners will be designed and fabricated at the outset of treatment. The individual aligners will then be available to the patient and/or treating professional so that the aligners may be worn and exchanged as the teeth progress through the expected successive arrangements. Usually, each individual aligner is worn for about two weeks corresponding to one stage of treatment. This period, of course, can vary from several days to several weeks or longer, depending on the individual treatment plan selected for the patient.

The present invention is concerned with those patients who do not progress through treatment as expected and planned. In some cases, an actual tooth arrangement achieved by a patient will differ from the expected tooth arrangement corresponding to the shape of a particular appliance. Such deviation from the expected treatment will usually become apparent when the patient tries to wear the next aligner in a series. If the actual tooth arrangement differs to any significant degree from that which was expected, the next aligner in series will typically not be able to seat properly over the teeth. Such inability to fit or seat on the teeth provides an indication that the actual tooth arrangement which has been achieved at that point in treatment differs from the expected tooth arrangement which should have been achieved after treatment with the immediately prior appliance.

The present invention provides methods for correcting such deviations in the planned and expected treatment path by providing at least one additional removable appliance which has a shape or a compliance selected to move the teeth from the actual (but deviant) tooth arrangement back to one of the predetermined successive tooth arrangements. The tooth arrangement to which the teeth are reconfigured will often be the arrangement to which they should have been at the end of the just completed stage. Alternatively, the arrangement could be any one of the successive stages, usually five stages or fewer beyond the just completed stage, more usually four stages or fewer, and typically no more than three stages beyond the just completed stage.

For the most minor deviations, it will be often be sufficient to provide an aligner or other tooth positioning appliance which has the same geometry as an aligner from the original set, usually as the next aligner in the series. While the aligner will have the same shape, it will be more compliant or elastic so that it can fit and seat over the teeth, even though the shape is further from the geometry of the actual tooth configuration than had been originally intended. The more compliant aligner can then bring the teeth back toward the target configuration for that stage of treatment. Optionally, two or more compliant aligners having the same geometry could be employed, where successive ones of the new aligners will be incrementally stiffer or more rigid to continue to move the teeth toward the target configuration.

The use of additional aligners having the same shape as an original aligner, but which are more compliant, is particularly advantageous since it simplifies design and fabrication of these aligners. The shape or geometry of the aligner would already have been planned during the initial treatment planning process (as described in detail in prior patent U.S. Pat. No. 5,975,893, which has been incorporated herein by reference), and it is necessary only to mold or otherwise fabricate the aligner out of materials having different elasticities. The ability to form aligners having different elasticities is described in detail in co-pending application No. 09/616,830, the full disclosure which has previously been incorporated herein by reference.

In some instances, however, it may not be possible and/or desirable to use aligners having the same geometry as an original aligner to bring the teeth back on to the intended treatment path. In such cases, it will be necessary to design one or more aligners having different shapes in order to move the teeth back from their actual configuration to a tooth arrangement corresponding to one of the appliances from the original set of appliances. Such treatment planning can be performed, for example, by the methods used for the original treatment planning as described in U.S. Pat. No. 5,975,893, the full disclosure of which has been incorporated herein by reference. That is, the actual tooth arrangement, i.e., the tooth arrangement which has been actually achieved in the treatment thus far, will be digitally modeled. Based on the digital model of the actual tooth configuration as a starting point, and a selected one of the target intermediate stages as an ending point, a series of one, two, three, four, or five, or more, new aligners or other positioning appliances can be designed using the computer-aided design protocols described in the patent. Once the new aligner designs are finalized, the digital models of the aligners can be used to fabricate actual aligners using the previously described methods.

For both compliant aligners and differently shaped aligners, the patient will wear the corrective aligners until the teeth have returned to an arrangement which allows an aligner from the original set of aligners to be worn and to move teeth to the next successive arrangement. Depending on the degree of deviation, it may take one, two, three, four, five, or even more, additional aligners or other positioning appliances to provide the desired correction. The corrective aligners or other appliances might be worn from several days to several weeks, or more, until the desired correction is achieved.

DESCRIPTION OF THE SPECIFIC EMBODIMENTS

Figure 1:
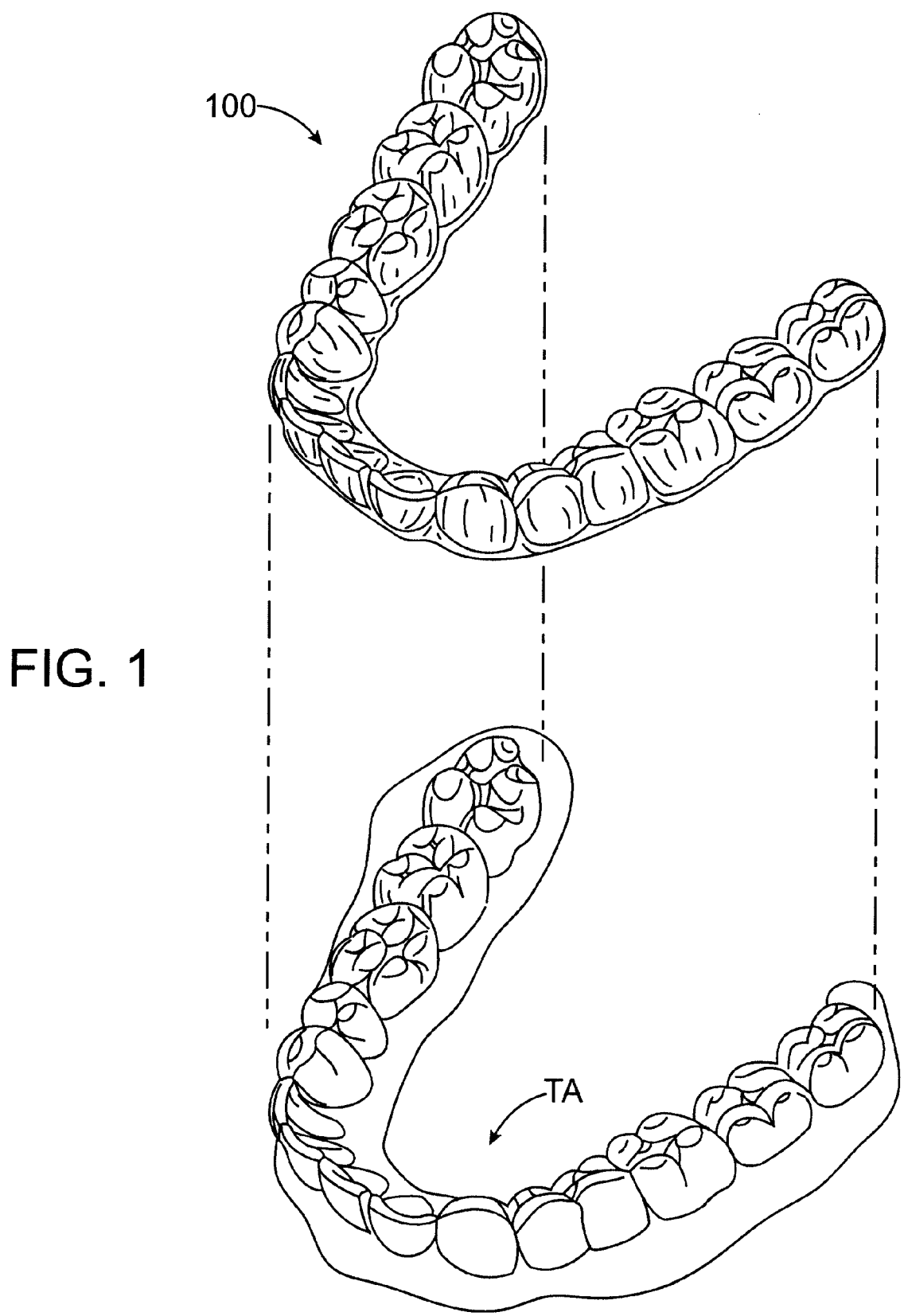
FIG. 1 illustrates an aligner according to the present invention and shows how the aligner is placed over a patient's teeth.

The present invention relies on the use of aligners 100 for positioning teeth in a tooth arrangement TA, as illustrated in FIG. 1. The aligner is a thin shell polymeric appliance of the type commercially available as part of the Invisalign® System available from Align Technology, Inc., Santa Clara, Calif. The planning and fabrication of such aligners is described in detail in issued U.S. Pat. No. 5,975,893, the full disclosure of which has previously been incorporated herein by reference. The aligners 100 are worn by a patient over the tooth arrangement for a sufficient time to rearrange the teeth to a desired subsequent tooth arrangement. A plurality of successive aligners are worn until an entire course of the treatment is completed.

Figure 2:
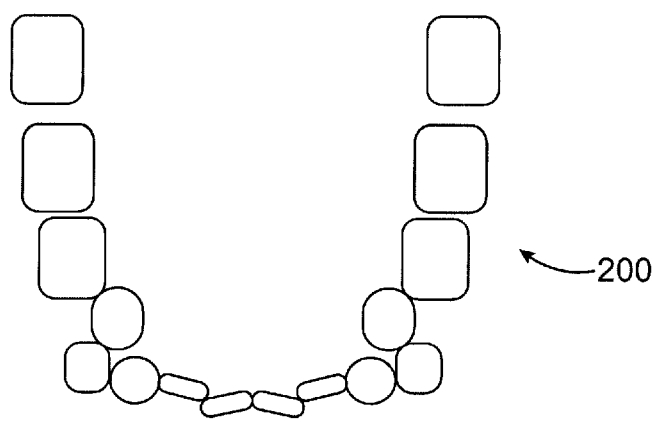
FIGS. 2–4 illustrate an exemplary series of three successive tooth arrangements which may be achieved with the aligners of FIG. 1.
Figure 3:
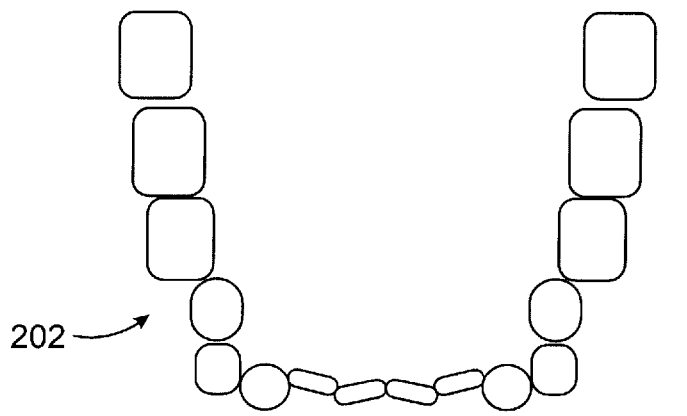
Figure 4:
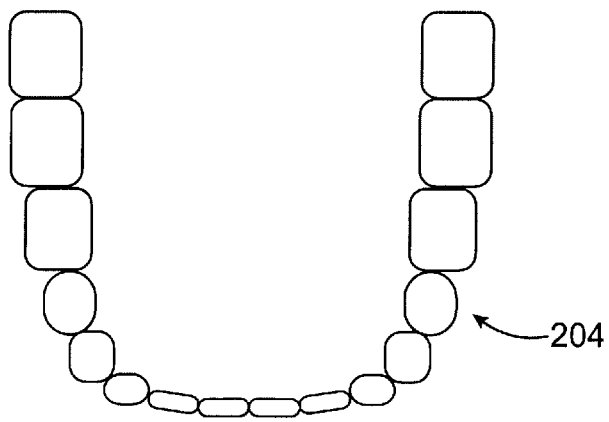

As shown in FIGS. 2–4, multiple stages of treatment will result in the teeth being rearranged. Tooth arrangement 200 shows the teeth in an initial configuration with significant misalignment. Tooth arrangement 202 shows the teeth of arrangement 200 partially reconfigured. Finally, tooth arrangement 204 illustrates the teeth in a desired final configuration. The methods for tooth arrangement of the present invention will typically rely on many more than three stages to achieve a desired reconfiguration. Usually, at least three stages will be required, more usually, at least five stages will be required, and typically 20 or more stages may be utilized.

Figure 5:
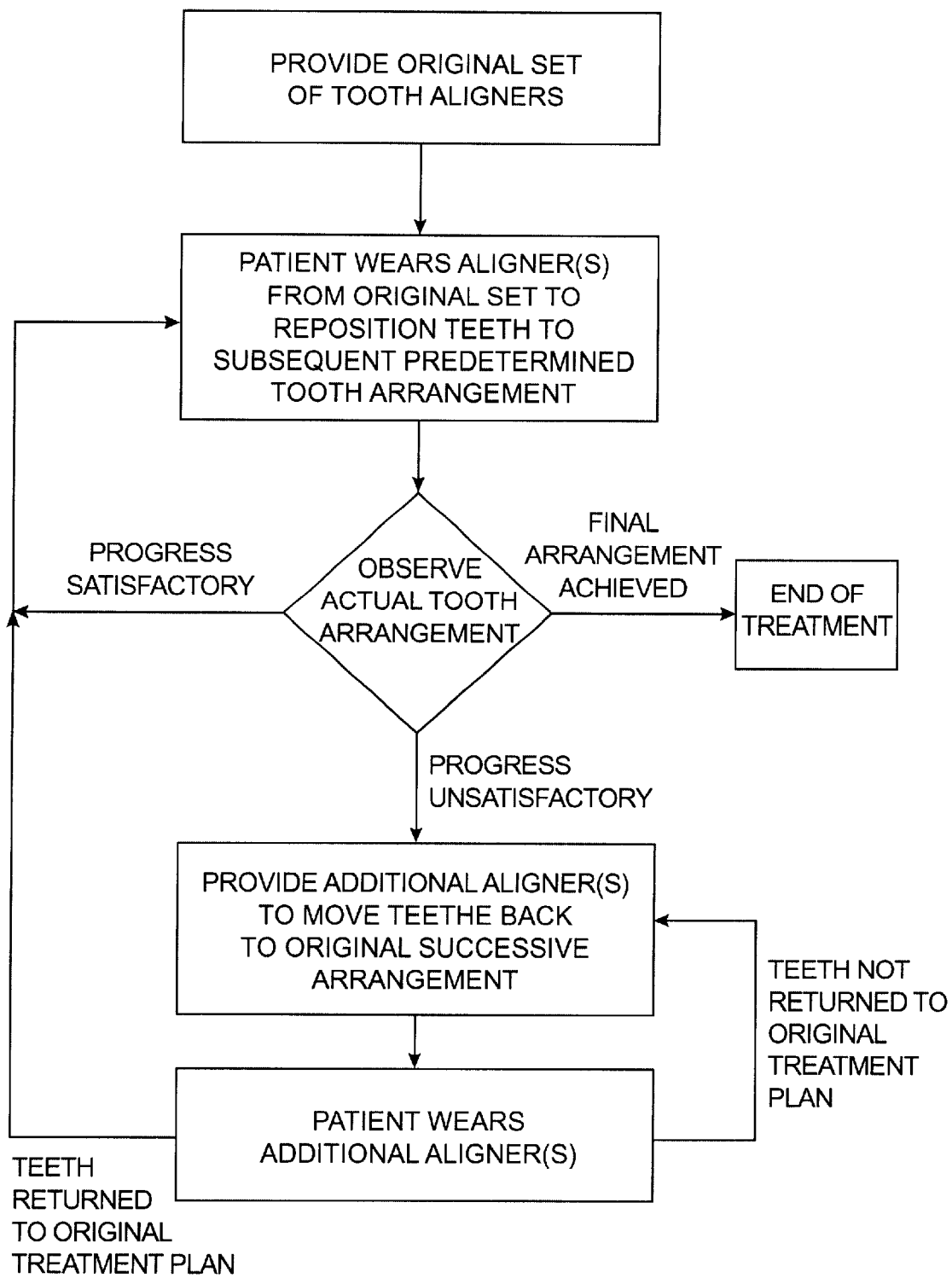
FIG. 5 is a decision tree illustrating an exemplary method according to the present invention.

If at any time during the originally planned course of treatment, the tooth arrangement deviates from a desired intermediate stage, i.e., an intermediate configuration is not achieved, it may be desirable to employ the methods of the present invention to correct such deviation and reconfigure the tooth arrangement to a desired predetermined intermediate stage. As shown in FIG. 5, the patient is initially treated with an original set of tooth aligners. The patient wears individual aligners from the original set to reposition teeth to subsequent predetermined tooth arrangements. Periodically during treatment, the patient or treating professional will observe the actual tooth arrangement achieved at any stage of treatment to see if it is satisfactory. If the progress is satisfactory, the patient will then wear the next aligner in the predetermined set of aligners. The process of confirming satisfactory progress and moving on the next tooth aligner may be repeated until the final desired tooth arrangement is achieved and the treatment ends.

In the case of some patients, however, the progress being achieved will not be satisfactory. For example, the next aligner in the predetermined original set of aligners may not seat or fit properly, indicating that the teeth have not moved to their desired target intermediate arrangement. In such cases, the present invention will provide additional aligner (s) or other reposition appliances to move the teeth back to an arrangement which was part of the original treatment path. The patient will then wear the additional aligner or aligners until the teeth are returned to the original treatment plan. If for any reason the use of the additional aligners is unsatisfactory, it may be appropriate to design and fabricate still further aligners or sets of aligners in order to correct the deviant treatment path. Once the teeth have been returned to an arrangement on the desired treatment path, treatment may then continue with the original aligner set which had been provided to the patient at the outset of treatment.

While the above is a complete description of the preferred embodiments of the invention, various alternatives, modifications, and equivalents may be used. Therefore, the above description should not be taken as limiting the scope of the invention which is defined by the appended claims.

What is claimed is:

1. In a method for repositioning teeth using an original set of removable positioning appliances shaped to move teeth through a plurality of predetermined successive arrangements corresponding to the shape of each appliance, a method for correcting midcourse deviations from the successive arrangements comprising:

determining that an actual tooth arrangement of a patient differs from an expected tooth arrangement corresponding to the shape of a particular appliance; and providing at least one additional removable appliance which has a shape or a compliance selected to move the teeth from the actual tooth arrangement back to one of the predetermined successive tooth arrangements.

2. A method as in claim 1, wherein determining comprises observing whether a particular predetermined removable appliance fits over the teeth at the expected corresponding tooth arrangement.

3. A method as in claim 1 or 2, wherein providing comprises providing a removable positioning appliance which has the same shape as an appliance from the original set but which is more compliant, wherein the more compliant appliance can be fitted over the teeth to move the teeth back to one of the predetermined successive arrangements.

4. A method as in claim 3, wherein providing comprises providing at least two removable positioning appliances which have the same shape as an appliance from the original set, wherein both of the additional appliances are more compliant than the original appliance and one of the additional appliance is more compliant than the other.

5. A method as in claim 1 or 2, wherein providing comprises providing a removable positioning appliance which has a shape different from the particular appliance, wherein the shape is selected to move the teeth from their actual arrangement back to one of the predetermined successive arrangements.

6. A method as in claim 5, wherein providing comprises providing at least two removable positioning appliances which have shapes selected to progressively reposition the teeth from the actual tooth arrangement back to one of the predetermined successive arrangements.

* * * * *